United States Patent [19]

Baker

[11] Patent Number: 4,866,994
[45] Date of Patent: Sep. 19, 1989

[54] REFRIGERATION SYSTEM OIL MEASUREMENT AND SAMPLING DEVICE

[75] Inventor: James A. Baker, Williamsville, N.Y.

[73] Assignee: General Motors Corporation, Detroit, Mich.

[21] Appl. No.: 220,285

[22] Filed: Jul. 18, 1988

[51] Int. Cl.[4] .................. G01N 1/10; G01N 25/14
[52] U.S. Cl. .................. 73/863.12; 73/61.1 R; 73/61.3; 73/863.86; 62/125; 62/127
[58] Field of Search .......... 73/863.12, 863.11, 863.57, 73/863.71, 864, 864.51, 864.63, 61.3, 61.1 R, 863.86; 324/57; 62/127, 125

[56] References Cited

U.S. PATENT DOCUMENTS

| 389,494 | 9/1888 | Block | 62/125 |
|---|---|---|---|
| 1,525,007 | 2/1925 | Shipley | 62/125 |
| 1,637,920 | 8/1920 | Shipley | 62/125 X |
| 2,577,598 | 12/1951 | Zwicki | 62/125 X |
| 3,050,449 | 8/1962 | Moore | 73/863.12 X |
| 3,153,913 | 10/1964 | Brody | 62/125 |
| 3,487,692 | 1/1970 | Cook, Jr. | 73/863.11 |
| 3,544,276 | 12/1970 | Merwitz, Sr. | 62/125 X |
| 3,638,476 | 2/1972 | Paterson et al. | 73/863.12 X |
| 3,985,624 | 10/1976 | Prevost et al. | 73/863.12 |
| 4,404,845 | 9/1983 | Schrenka | 73/863.12 X |
| 4,610,169 | 9/1986 | Clavell, Jr. | 73/863.12 |

FOREIGN PATENT DOCUMENTS 368487 3/1973 U.S.S.R. .................. 62/125

Primary Examiner—Tom Noland
Attorney, Agent, or Firm—R. L. Phillips

[57] ABSTRACT

A sample cell connected through valving to a refrigeration system allows a prescribed mass of refrigerant with entrained oil to be collected and the refrigerant to be vaporized and returned to the system while leaving the oil in a graduated measuring tube. The sample cell has transparent upper and lower portions with graduated bores for measurement of the original sample and the oil residue, and an aluminum middle portion also containing a bore for conducting heat from the ambient air to the refrigerant to assist in the vaporization as well as for normalizing the temperature of the sample during filling.

2 Claims, 1 Drawing Sheet

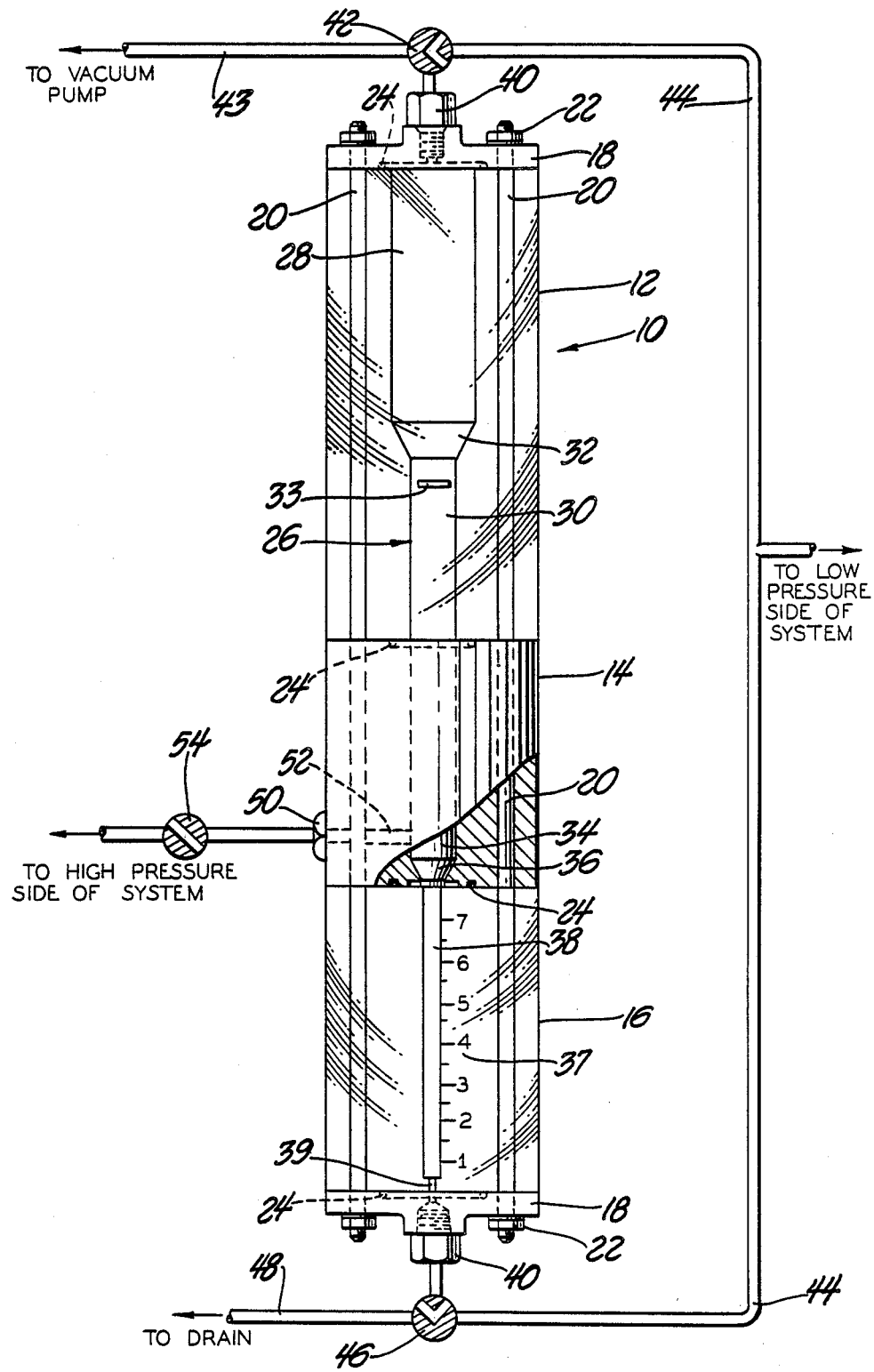

REFRIGERATION SYSTEM OIL MEASUREMENT AND SAMPLING DEVICE

FIELD OF THE INVENTION

This invention relates to a sampling device for refrigeration systems and particularly to such a device for measuring the oil content of refrigerant.

BACKGROUND OF THE INVENTION

Refrigeration systems typically contain oil in the range of 0 to 8 percent mixed in the refrigerant for lubrication purposes. It is useful to be able to analyze the working fluid to determine the amount of oil present. It is also useful to be able to observe the fluid to determine the presence of other matter such as metal particles which are indicative of compressor wear. On the other hand, such measurements and observations should not result in loss of refrigerant from the system and should not interfere with the system operation.

SUMMARY OF THE INVENTION

It is therefore an object of the invention to provide a sampling device for coupling to a refrigeration system for withdrawing a sample of refrigerant and for separating the oil entrained therein for measurement. It is a further object to provide such a device with the capability of returning the refrigerant to the system.

The invention is carried out by a sampling device for use with a refrigeration system having a refrigerant and oil entrained therein, comprising; an elongated reservoir having a stepped bore therein for receiving refrigerant and oil carried thereby, first valve means for coupling the reservoir to the refrigeration system to admit liquid refrigerant to the reservoir, second valve means for coupling the reservoir to the refrigeration system to evacuate vaporized refrigerant from the reservoir, means for supplying heat to the refrigerant in the bore to facilitate vaporization of the refrigerant, and means for measuring the oil remaining in the bore after vaporization.

BRIEF DESCRIPTION OF THE DRAWINGS

The above and other advantages of the invention will become more apparent from the following description taken in conjunction with the accompanying drawing wherein the single figure is an elevation of a sampling device according to the invention.

DESCRIPTION OF THE PREFERRED EMBODIMENT

Referring to the drawings, the sampling device 10 is an elongated cylinder comprising an upper section 12, a middle section 14, a lower section 16, and end caps 18. The assembly is held together by four equally spaced steel tie rods 20 extending longitudinally through the cylinder. Each rod 20 has a threaded end receiving a nut 22. Each end of the middle section 14 as well as each end cap 18 has an annular groove 24 containing an O-ring seal so that the sections, when forced together by the tie rods 20, are connected in a leak free manner.

A stepped bore forming a reservoir 26 on the cylinder axis extends through all the sections. In the upper section 12 the reservoir has a large diameter buffer bore 28 and an intermediate diameter bore 30 interconnected by a tapered section 32. The upper section 12 is made of a transparent acrylic material and has a fill mark 33 either inside the bore 30 or outside the section. The middle section 14 is aluminum or other good heat conducting material and has an intermediate diameter bore 34 forming a continuation of the bore 30 of the upper section. A taper 36 at the bottom of the middle section connects to a small diameter bore 38 or measuring tube in the lower section 16. The lower section 16 is made of a transparent acrylic material and has graduation indices or a scale 37 along the bore 38 marked in percent of the original sample size or in grams. By choosing a suitable ratio of bore diameters a very small quantity can be easily read on the scale. It has been found that for a sample of 50 grams, a device about 450 mm long with an intermediate bore 30 diameter of about 20 mm and a small bore 38 diameter of about 7 mm is satisfactory and allows measurement to a fraction of one percent of sample mass. The small bore 38 terminates in a smaller passage 39 which extends to the lower end cap 18.

Each end cap 18 is centrally apertured and is threaded to receive an adapter fitting 40 which is in communication with the reservoir 26. The upper fitting is coupled to a three-way valve 42 which is connected to an A/D (accumulator/dehydrator) line 44 which goes to the combination accumulator and dehydrator unit at the low pressure side of the refrigeration system and to a vacuum line 43 which is connected to a vacuum pump, not shown. The lower fitting is coupled to a three-way valve 46 which is connected to a drain 48 and to the A/D line 44. A third fitting 50 is attached to the side of the middle section 14 and is connected by a passage 52 to the bore 34. A two-way valve 54 coupled to the fitting 50 is connected to a liquid line 56 or the high pressure side of the refrigeration system.

In use, it is desired to sample a fixed amount of working fluid during operation of the refrigeration system and measure the oil content as well as to observe or analyze the fluid for a determination of other content such as metal particles. Starting with an empty reservoir the valve 54 is opened to admit fluid through the passage 52 in the aluminum section to the bores 30 and 38. The temperature of the fluid in the line 56 may be much above or below room temperature. During filling of the reservoir the fluid attains a temperature near room temperature due to the heat transfer property of the aluminum. This eliminates any significant variable due to thermal expansion so that the sample has a prescribed mass when the level reaches the fill mark 33. Then the valve 54 is closed and the valve 42 is opened to apply the suction of line 44 to the reservoir. The refrigerant in the sample is allowed to vaporize and the vapor is drawn out through the valve 42 and the A/D line 44. Heat conducted from the ambient air to the reservoir by the aluminum section assists in the vaporization which takes only a few minutes. Vigorous boiling may occur upon reducing the pressure and any foaming or splashing which takes place is accommodated in the large diameter buffer bore 28 so that no liquid is drawn out of the reservoir. Within about ten minutes the vapor pressure will reach the pressure of the A/D line and the remaining fluid will be oil with a substantial amount of refrigerant dissolved therein. To degas the oil to remove the remaining refrigerant the valve 42 is operated to couple the vacuum line 43 to the reservoir. After about ten minutes the refrigerant will all have been removed and the residue is the oil and other material entrained in the working fluid and its level will register on the scale 37 of the small bore or measuring tube 38. After the amount of oil is read it is discharged from the reservoir by opening the valve 46 to the A/D line 44 to return the oil to the system or by opening the valve 46 to the drain 48 for collecting the oil sample in a sample tube for further analysis.

After making the measurement and draining the oil, any residual oil is easily removed by filling the reservoir with refrigerant from the liquid line 56 and then returning it to the system via the line 44.

It will thus be seen that the sampling and measurement device provides an inexpensive tool for easy measurement of oil in circulating refrigerant without permanent loss of the refrigerant sample and with the option of returning the oil to the system or removing it for further analysis.

The embodiments of the invention in which an exclusive property or privilege is claimed are defined as follows:

1. A sampling device for use with a refrigeration system having a refrigerant and oil entrained therein, comprising;
    an elongated reservoir having a stepped bore therein for receiving refrigerant and oil carried thereby, the reservoir comprising a large bore diameter upper section having an index marking the fill level of the reservoir and a small bore diameter lower section having graduation marks for oil level measurement, the upper and lower sections comprising transparent material to allow observation of the contents,
    first valve means for coupling the reservoir to the refrigeration system to admit liquid refrigerant to the reservoir,
    second valve means for selectively coupling the reservoir to the low pressure side of the refrigeration system or to a vacuum line to evacuate vaporized refrigerant from the reservoir, and
    means for supplying heat to the refrigerant in the bore to facilitate vaporization of the refrigerant.

2. The invention as defined in claim 1 wherein the means for supplying heat to the refrigerant comprises a middle section of the reservoir between the upper section and the lower section, the middle section comprising heat conducting material to conduct heat from ambient air to the refrigerant.

* * * * *